(12) United States Patent
Akimoto et al.

(10) Patent No.: US 6,500,679 B2
(45) Date of Patent: Dec. 31, 2002

(54) FLUORESCENCE-ENHANCED CHIP

(75) Inventors: Takuo Akimoto, Musashino (JP); Takeo Tanaami, Musashino (JP); Kazunori Ikebukuro, Koganei (JP); Kazuyoshi Yano, Tokyo (JP); Isao Karube, Tokyo (JP)

(73) Assignees: Yokogawa Electric Corporation, Tokyo (JP); Center for Advanced Science and Technology Incubation, LTD, Tokyo (JP)

(*) Notice: Subject to any disclaimer, the term of this patent is extended or adjusted under 35 U.S.C. 154(b) by 0 days.

(21) Appl. No.: 10/090,518

(22) Filed: Mar. 4, 2002

(65) Prior Publication Data
US 2002/0132376 A1 Sep. 19, 2002

(30) Foreign Application Priority Data

Mar. 15, 2001 (JP) .................................. 2001-073378
Feb. 12, 2002 (JP) .................................. 2002-033813

(51) Int. Cl.[7] .......................... H01L 21/00; H01L 21/20
(52) U.S. Cl. ...................... 438/3; 438/22; 438/34; 438/73
(58) Field of Search .......................... 438/3, 34, 46, 438/63, 89, 962, 22, 73; 257/668

(56) References Cited

U.S. PATENT DOCUMENTS

| | | | | |
|---|---|---|---|---|
| 4,081,716 A | * | 3/1978 | Uemura ....................... | 313/497 |
| 4,723,837 A | * | 2/1988 | Masubuchi ................... | 257/30 |
| 5,568,417 A | * | 10/1996 | Furuki et al. ................ | 365/106 |
| 5,882,779 A | * | 3/1999 | Lawandy ..................... | 257/102 |
| 6,410,166 B1 | * | 6/2002 | Takahashi et al. ........... | 313/504 |
| 2001/0013755 A1 | * | 8/2001 | Ogawa et al. ............... | 313/496 |

* cited by examiner

*Primary Examiner*—Michael S. Lebentritt
(74) *Attorney, Agent, or Firm*—Moonray Kojima

(57) ABSTRACT

The present invention aims to achieve a chip having a construction in which each film of metal, dielectric, and fluorescent material is stacked on a glass substrate 1. Such a construction can enhance the intensity of fluorescence emitted from a fluorescent material owing to the interaction between the fluorescent material and the light propagation mode in that construction.

1 Claim, 3 Drawing Sheets

FLUORESCENCE-ENHANCED CHIP

BACKGROUND OF THE INVENTION

1. Field of the Invention

The present invention relates to a fluorescence-enhanced chip that enhances the intensity of fluorescence.

2. Description of the Prior Art

Techniques for measuring the intensity of fluorescence emitted from fluorescent materials are important in the field of immunology and nucleic acid detection. In the case of detecting protein or nucleic acids or the like (hereinafter simply called 'nucleic acid'), a nucleic acid of interest is labeled with a fluorescent material in advance, then this nucleic acid to be detected is identified by its fluorescence emission generated by the irradiation of excitation light.

In this case, the intensity of fluorescence is an index for quantifying the nucleic acid of interest. Accordingly, if the same quantities of fluorescent materials are used, the more intense the detected fluorescence intensity, the higher the detection sensitivity in that system. That is, extremely smaller quantities of protein or nucleic acid can be quantified.

For this purpose, enhancing fluorescence from fluorescent materials of equal quantity is extremely significant in immunology and the detection of nucleic acid.

U.S. Pat. No. 4,649,280 mentions a fluorescence-enhanced chip, in which the intensity of fluorescence generated from fluorescent material 4 can be enhanced as a construction having a stack of metal 2, dielectric 3, and fluorescent material 4 films on glass substrate 1 as shown in FIG. 1.

It is disclosed that the intensity of fluorescence in this case is related to the thickness d of dielectric film 3, and lithium fluoride (LiF) is used as dielectric film 3.

However, in such conventional fluorescence-enhanced chips, there are the problems that the dielectric LiF used is expensive, cannot easily be used for general purposes, and is vulnerable to corrosion.

SUMMARY OF THE INVENTION

The objective of the present invention is to solve the above problems and to realize a fluorescence-enhanced chip that is cheap, can easily be used for general purposes, and also has excellent corrosion resistance. This can be done by employing silicon dioxide ($SiO_2$), that is cheap, can easily be used for general purposes, and also has excellent corrosion resistance, as the above dielectric.

In order to achieve such a purpose, the present invention provides a fluorescence-enhanced chip that is composed of a glass substrate and stacked films of metal, dielectric, and fluorescent material and can enhance the intensity of fluorescence generated from light-excited fluorescent material;

employs $SiO_2$ having the film thickness of 330 nm or less as the above dielectric; and uses silver (Ag) or aluminum (Al) as the above metal.

According to such configuration, a fluorescence-enhanced chip that is cheap and excellent in corrosion resistance can easily be realized because $SiO_2$, which is cheap, can easily be used for general purposes, and has excellent corrosion resistance, is used as the dielectric.

DESCRIPTION OF THE PREFERRED EMBODIMENTS

Figure 2:
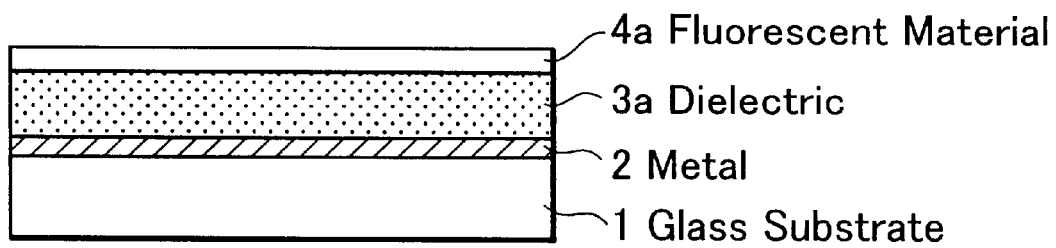
FIG. 2 shows a schematic diagram indicating the configuration of the fluorescence-enhanced chip for an embodiment of the present invention.

The present invention will be described below in detail using the drawings. FIG. 2 shows a schematic diagram indicating the configuration of the fluorescence-enhanced chip for an embodiment of the present invention. Enhancement of the intensity of fluorescence from a fluorescent material in such a chip depends on the interactions between the fluorescent material and the light propagation mode in that construction.

In FIG. 2, numeral 1 denotes a glass substrate, numeral 2 a metal, numeral 3a a dielectric, and numeral 4a a fluorescent material used for labeling a protein or nucleic acid of interest. As metal 2, for example, silver (Ag) or aluminum (Al) is used and dielectric 3a consists of $SiO_2$.

Figure 1:
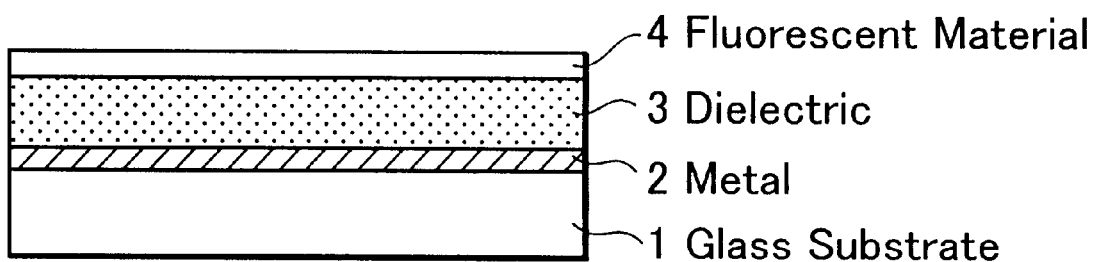
FIG. 1 shows an example of a schematic diagram indicating the configuration of a conventional fluorescence-enhanced chip.

In the configuration of this chip, metal 2, dielectric 3a, and fluorescent material 4a are stacked on glass substrate 1, similar to that shown in FIG. 1. For fluorescent material 4a, fluorescein isothiocyanate (FITC) of concentration 25 µg/ml dissolved into purified water is used, and this FITC solution is dropped onto dielectric 3a using a micropipette and dried to form fluorescent material 4a.

Figure 3:
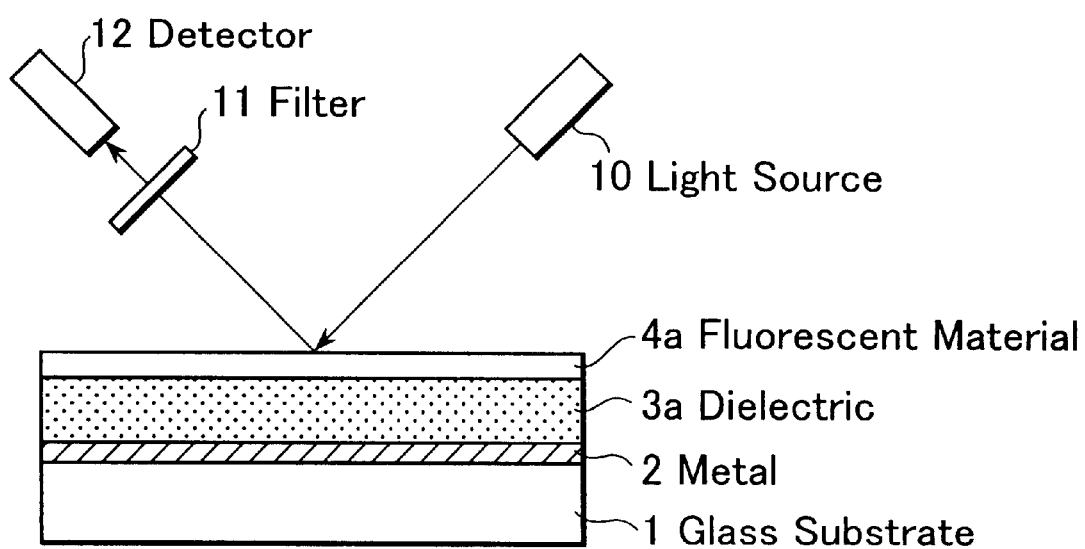
FIG. 3 shows a schematic diagram indicating the configuration for measuring the intensity of fluorescence from a fluorescence-enhanced chip.

The fluorescence-enhanced chip having such a construction is described below for the case where its intensity of fluorescence is measured in the following system shown in FIG. 3.

Argon (Ar) laser having the wavelength of 488 nm irradiates fluorescent material 4a from light source 10. The fluorescence emitted from fluorescent material 4a is detected to measure the intensity of fluorescence by detector 12 after being passed through band-pass filter 11 for wavelength 530 nm.

Figure 4:
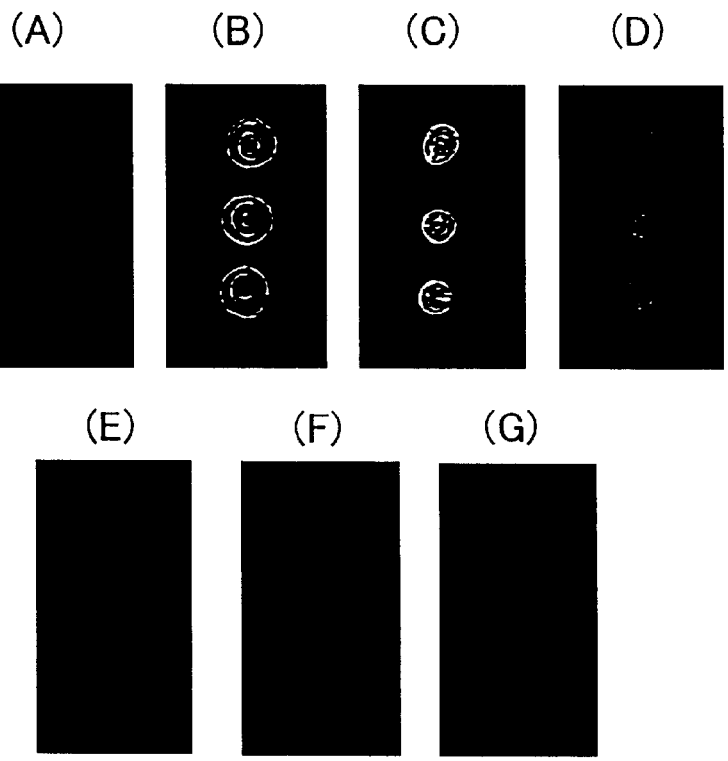
FIG. 4 indicates several examples of observation of the intensities of fluorescence in several chips.

FIG. 4 shows examples of observing the intensity of fluorescence based on various chips. FIG. 4 (A) indicates the result in the case where the $SiO_2$ film having the thickness of 200 nm is formed on glass substrate 1 shown in FIG. 2, on which metal film 2 is not formed, and FITC is dropped onto the $SiO_2$.

FIG. 4 (B) to (G) indicate results similar to the above using substrates having the same construction as that shown in FIG. 2, the thickness of $SiO_2$ films being 44, 48, 132, 176, 200, and 244 nm respectively. The thickness of metal 2, that is Ag film, is about 50 nm in each substrate.

Figure 5:
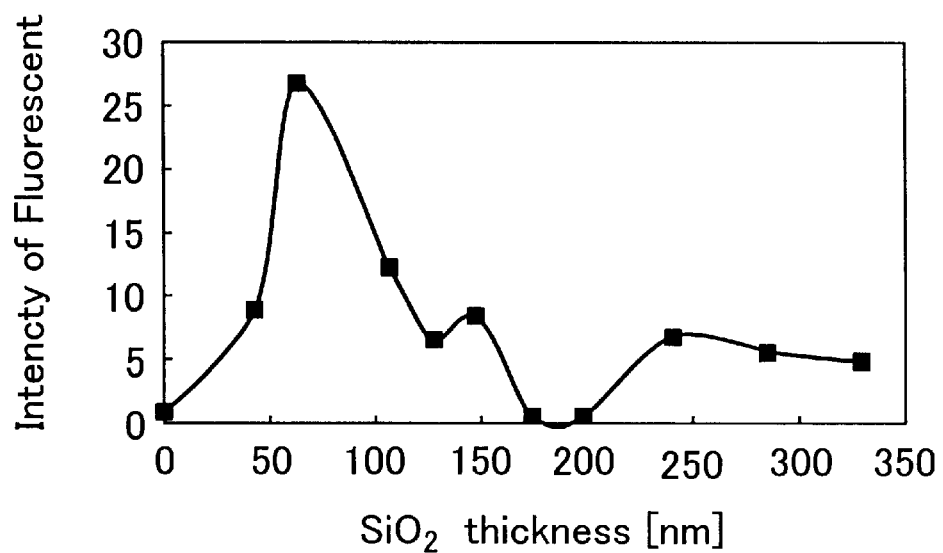
FIG. 5 is a graph indicating the relationship between the relative fluorescence intensities and the corresponding thickness of dielectric $SiO_2$.

As is apparent from the results shown in FIG. 4, the intensity of fluorescence varies with the thickness of $SiO_2$ film. FIG. 5 shows the relationship between the relative intensity of fluorescence, I, and the thickness of $SiO_2$ film in this case.

The relative intensity of fluorescence I is defined as shown below.

$$I = I_r / I_o$$

where, $I_r$ denotes the value of the intensity of fluorescence at each $SiO_2$ film thickness, and $I_o$ denotes the value of the intensity of fluorescence for FIG. 4(A).

As seen in FIG. 5, the maximum intensity of fluorescence occurs at the thickness of $SiO_2$ in the vicinity of 65 nm. Furthermore, the intensity of fluorescence in the above case is enhanced by about 27-fold compared with the intensity in the case of glass substrate 1 only.

In addition, the present invention is not limited to the above embodiment but may include many further changes and versions without departing from the scope of spirit thereof.

For example, the fluorescent reagent is not limited to FITC, but Rhodamin or the like may also be used. Although the $SiO_2$ film thickness of 65 nm is optimum, it is not necessary to control the thickness exactly to this value. Even film thickness values other than the above can also provide excellent enhancement effects as is apparent from FIG. 5.

As described above, according to the present invention, a fluorescence-enhanced chip, which is cheap, can easily be used for general purposes, and has excellent corrosion resistance, can easily be realized.

What is claimed is:

1. A fluorescence-enhanced chip that is composed of a glass substrate and stacked films of metal, dielectric, and fluorescent material on said substrate, and that can enhance the intensity of fluorescence generated from said light-excited fluorescent material;

wherein said dielectric is composed of a silicon dioxide ($SiO_2$) having the film thickness of 330 nm or less; and wherein said metal comprises silver (Ag) or aluminum (Al).

* * * * *